United States Patent
Shirakawabe et al.

(10) Patent No.: US 6,953,519 B2
(45) Date of Patent: Oct. 11, 2005

(54) METHOD OF MANUFACTURING THE MULTI-TIP PROBE, A MULTI-TIP PROBE, AND SURFACE CHARACTERISTIC ANALYSIS APPARATUS

(75) Inventors: Yoshiharu Shirakawabe, Chiba (JP); Hiroshi Takahashi, Chiba (JP); Tadashi Arai, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/651,526

(22) Filed: Aug. 29, 2003

(65) Prior Publication Data

US 2004/0074288 A1 Apr. 22, 2004

(30) Foreign Application Priority Data

Aug. 30, 2002 (JP) ........................................ 2002-254880

(51) Int. Cl.⁷ .............................. C23C 14/32; C23F 1/00
(52) U.S. Cl. ............................ 204/192.32; 204/192.34; 216/66; 216/94; 427/523; 427/526; 427/531; 427/595
(58) Field of Search ....................... 204/192.32, 192.34; 216/66, 94; 427/523, 526, 531, 595

(56) References Cited

U.S. PATENT DOCUMENTS 6,668,628 B2 * 12/2003 Hantschel et al. ............ 73/105

FOREIGN PATENT DOCUMENTS

JP          09-127139       *   5/1997

* cited by examiner

*Primary Examiner*—Rodney G. McDonald
(74) *Attorney, Agent, or Firm*—Adams & Wilks (57) ABSTRACT

In order to establish processing techniques capable of making multi-tip probes with sub-micron intervals and provide such microscopic multi-tip probes, there is provided an outermost surface analysis apparatus for semiconductor devices etc. provided with a function for enabling positioning to be performed in such a manner that there is no influence on measurement in electrical measurements at an extremely small region using this microscopic multi-tip probe, and there are provided the steps of making a cantilever 1 formed with a plurality of electrodes 3 using lithographic techniques, and forming microscopic electrodes 6 minute in pitch by sputtering or gas-assisted etching a distal end of the cantilever 1 using a focused charged particle beam or using CVD.

29 Claims, 9 Drawing Sheets

A-A' CROSS-SECTION

FIG.7C

BEFORE PROCESSING

FIG.7E

FIB PROCESS 1

FIG.7G

FIB PROCESS 2

SAMPLE A

FIG.9B

SAMPLE B

FIG.9C

SAMPLE C

FIG.9D

STAGE MOVEMENT

FIG.11

METHOD OF MANUFACTURING THE MULTI-TIP PROBE, A MULTI-TIP PROBE, AND SURFACE CHARACTERISTIC ANALYSIS APPARATUS

BACKGROUND OF THE INVENTION

1. Field of the Invention

The present invention relates to a scanning probe microscope according to the four-tip probe method which the microscope is to be used in, for example, semiconductor process evaluation, and also to a probe suitable for analyzing an ultra-surface region of a sample when used in the scanning probe microscope.

2. Description of Related Art

The invention of the transistor evolved from studies of the electrical characteristics of a semiconductor surface, particularly the surface electron state. However, with respect to electrical conduction due to the state of surface electrons themselves, many points have been left unanalyzed until today. This "surface state conduction" is extremely difficult to measure because electricity runs only in one or two electron layers of a crystal surface. However, thanks to the development of new measuring and inspecting techniques, such as a four-tip probe scanning tunnel microscope operating in an ultra-high vacuum and a microscopic four-tip probe, direct measurement of the surface state conduction has become possible and very interesting conduction characteristics have become revealed as a result. To this end, it has been determined that the electron state of a semiconductor surface has a unique characteristic totally different from that of the bulk state. In the electron device field, apparatuses of this type will play an important role in research and development of electron devices.

Figure 10A:
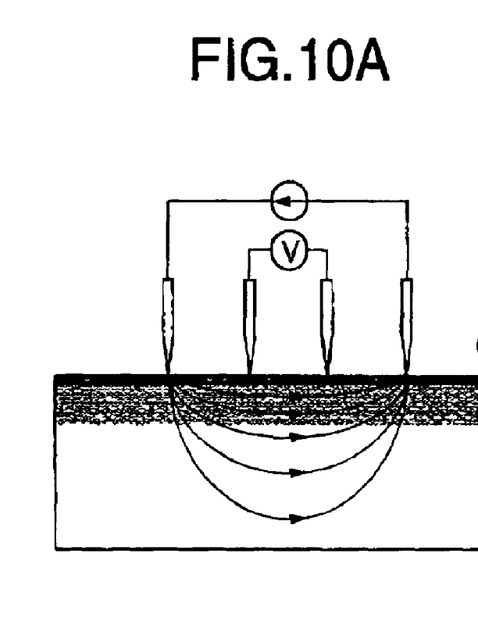
FIGS. 10A–10B are views showing a correlation between the inter-probe tip distance and the depth of detection to a sample.
Figure 10B:
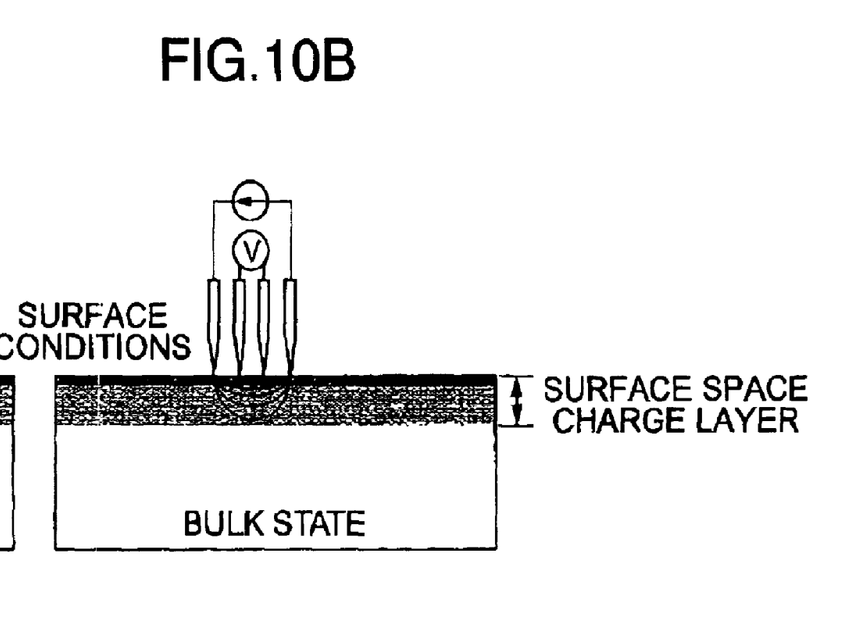

In an evaluating apparatus using a scanning tunnel microscope according to the four-tip probe method, four probe tips are arranged linearly at regular distances, a current is caused to flow into a sample from the outer two of the probe tips, and a voltage drop caused due to the electrical resistance of the sample is measured by the inner two of the probe tips. At such time, because there is only a very slight current flowing in these probe tips, only a voltage drop V on the sample can be measured without influence of the contact resistance at a point of contact of the probe tips with the sample. An electrical resistance according to the four-tip probe method is obtained by R=V/I where I is a measured current. As shown in FIGS. 10A and 10B there is a correlation between the inter-probe-tip distance and the depth of probing into a sample. In order to obtain information of the ultra-surface of the sample, it is essential to arrange the probes at a the corresponding narrow distances shown in FIG. 10B. In the related art, however, there is a limit in processing. This is to say that the diameter of the individual probe tip has served as a restriction so that a probe having a probe-tip pitch of several μm could not be manufactured.

Conventionally, four-tip probes whose inter-tip distance is in the order of millimeters to centimeters have been used, and many studies on this type of probe were carried out. However, these conventional probes cannot be applied to surface analysis of semiconductor devices. Recently, an undergraduate research group of Tokyo University released a report (Applied Physics, 70th Volume, 10th Issue, 2001) on measurement of electrical resistance of a silicon crystal surfaces using a microscopic four-tip probe of a several m pitch manufactured utilizing silicon micro-processing technology, such as ordinary lithography. For analyzing the outermost or uppermost device-surface, however, this several μm inter-tip distance is inadequate to achieve proper performance. An inter-tip distance of at most 1 μm or less is needed for doing so. Even if the above-mentioned silicon micro-processing technology is employed, it is difficult to manufacture a four-tip probe having an inter-tip distance of a such a sub-micron order.

In a further related art study, positioning of measuring points on an object surface is carried out using an optical microscope. However, because a required measuring region for analyzing the outermost or uppermost device-surface is extremely small, it is difficult to achieve positioning using the conventional optical microscope and, as an alternative means, a new observation technique, such as a scanning electron microscope (SEM) and an atomic force microscope (AFM) has been required. When an SEM is used, a sample is always irradiated with electrons during observation. This may produce noise and render accurate measurement of electricity impossible. On the other hand, in the case of an AFM, observation can be realized either in an ordinary atmospheric environment or a special atmospheric environment. However, when a multi-tip probe itself is used also as an image-obtaining probe, this may be a hindrance to accurate measurement for reasons such as (1) it is difficult to perform image analysis from signals detected by a plurality of probe tips arranged in a row and (2) the image is contaminated or otherwise damaged by scanning. Further, in the conventional AFM, it is a common practice to employ the light leverage method in which a mirror is mounted on a cantilever to detect displacement. In this case, a sample is irradiated with laser light. Because laser light serves as an excitation energy source to cause surface atoms to enter an excited state, this has a considerable effect on the movement of electrons on a device surface and therefore also impedes accurate measurement of electricity. Alternatively, waves serving as excitation light can be removed by wavelength cutoff using a filter. However, this alternative cannot realize observation in a perfect dark field and would often encounter problems, such as decreases in sensitivity due to attenuation of light intensity.

SUMMARY OF THE INVENTION

It is accordingly an object of the present invention to provide a a processing method to form a microscopic multi-tip probe whose inter-tip distance is on a sub-micron order, and to thereby provide such a microscopic multi-tip probe. Another object of the present invention is to provide an ultra-surface analyzing apparatus for analyzing the ultra-surface of a semiconductor device, the apparatus of having a function of positioning that does not influence electricity measurement in an extremely small region using the microscopic multi-tip probe.

The multi-tip probe manufacturing method of the present invention comprises the steps of making a cantilever using lithographic techniques and forming microscopic electrodes at a distal end of the cantilever by sputtering and gas-assisted etching processing using a focused charge particle beam.

This method of manufacturing a multi-tip probe of the present invention comprises the steps of, after making a cantilever using lithographic techniques, performing separation so as to form a plurality of lead portions using lithographic techniques on the cantilever and forming a shunt area at the distal end, and processing the shunt area of the distal end using a focused charged particle beam using sputtering or gas-assisted etching, exposure to X-rays using a stopper, mask aligner, and Synchrotron Orbital Radiation (SOR), or by electron beam rendering and etching so as to form microscopic electrodes.

Further, the method of manufacturing a multi-tip probe of the present invention comprises the steps of, after making a cantilever using lithographic techniques, performing separation so as to form a plurality of lead portions using lithographic techniques on the cantilever, and blasting the distal end of the cantilever with a source gas and irradiating with a focused charged particle beam so as to form microscopic electrodes.

In order to provide the surface characteristic analysis device of the present invention with functions where the microscopic multi-tip probes are put into a non-contact state and an observed image is obtained for a sample surface using an AFM function, a measurement region is specified from the observed image, and the multi-tip probes are positioned at the specified regions and contact is made, drive means are provided for positioning probe positions of a cantilever having a microscopic multi-tip probe of a pitch of 1□m or less at a distal end and a cantilever for AFM use having a dedicated probe at a distal end with a known prescribed gap there between and driving the probes independently so as to be in contact/non-contact states with respect to the sample surface.

One of a bi-metal actuator, a comb-shaped electrostatic actuator, or a piezoelectric microactuator is adopted as the mesas for driving in a contact/non-contact state.

A self-detecting method where a strain gauge is installed at the cantilever is adopted to enable measurement in a dark field state.

A multi-tip probe of the present invention comprises a cantilever formed using lithographic techniques, a plurality of lead portions formed on the cantilever, and a plurality of electrodes connected to each of the lead portions so that the pitch between the electrodes is narrower than pitch between the lead portions.

The multi-tip probe of the present invention may have a configuration provided with a convex bank at the region where the electrode of the cantilever are formed or may be provided with probes at the electrodes.

DETAILED DESCRIPTION OF THE PRESENT INVENTION

In a scanning tunnel microscope according to the four-tip probe method to be used for semiconductor process evaluation, there is the correlation shown in FIGS. 10A and 10B between the inter-tip distance and the depth of probing into a sample, as described above. Moreover, in order to obtain information of an ultra surface, it is essential to arrange the probe tips at the corresponding narrow distance as shown in FIG. 10B of the figure. In the related art, there is a limit in processing, and as the diameter of the individual probe tip is restricted, an 8 $\mu$m pitch electrode is reported. However, a probe having an inter-tip distance on the order of sub-microns cannot be manufactured. Consequently, the present invention is intended firstly to fabricate a cantilever by the related method and then to form a probe having a microscopic inter-tip distance by processing a distal end portion of the cantilever utilizing nano-processing technology.

For example, according to one technique, a single micro cantilever is fabricated by coating a substrate of silicon with a conductive thin film or by implanting ions into a substrate to make the substrate conductive. The resulting micro cantilever has a multi-tip conductive portion whose tips are spaced one from another and a shunt area formed on a distal end portion of the cantilever into which area the tips of the conductive portion merge. In order to obtain a less than 1 $\mu$m tip pitch, comb-shaped electrodes that are separated from each other are formed in the shunt area of the distal end portion of the cantilever by an etching process, such as sputter etching or gas assist etching using, for example, a focused ion beam (FIB) apparatus. The comb-shaped electrodes are used as a multi-tip probe. According to another technique, a single cantilever having a multi-tip conductive portion whose tips are spaced one from another and a non-conductive area formed at a distal end portion of the cantilever is fabricated using photolithographic processes. Further, the above-described structure is obtained by depositing metal or carbon on the distal end portion of the cantilever, which is wired by a patch process, at desired distances by chemical vapor deposition (CVD) using an FIB apparatus. The microscopic multi-tip conductive portions may be formed by making the silicon, i.e. the cantilever, conductive using ion implantation techniques through irradiation with a beam rather than by CVD. It is possible to make processing time shorter by making lead portions that are not required in the microscopic processing as conductors for use with the multi-tip probe etc. in advance.

In another alternative, a needle-shaped electrode may be manufactured which is comprised of not only the comb-shaped electrode, but also by laminating or depositing a conductive substance (such as carbon or tungsten) on the distal end portion of the electrode. This electrode can make contact with a sample in an improved manner. In the manufacture of the electrode by processing the deposited metal using an FIB apparatus, an ultra-microscopic multi-tip probe whose inter-tip distance is several hundreds to several nm can be formed with ease, depending on the metal film thickness. In the foregoing description, an FIB is used as a source of a charged particle beam. Alternatively, however, the processing, which is gas assist etching or CVD, may be realized using an apparatus using an electron beam.

Further, for analyzing the outermost or uppermost surface of a device, it is essential to specify the position of the device surface. Conventionally, the positioning is carried out by obtaining an observed image of the device surface of a sample on an optical microscope. However, because a measuring region is extremely small, specifying the device surface position using an optical microscope is difficult to achieve, requiring, as an alternative means, a new observation technique, such as a high-resolution scanning electron microscope (SEM) or an atomic force microscope (AFM). When an SEM is used, electrons are irradiated to a sample always during observation as mentioned above. This would be a cause for noise so that accurate measurement of electricity cannot be performed. For this reason, this type of surface observation apparatus is inconvenient to use. When an observed image is obtained by an AFM, a laser to be used for measurement of displacement and serving as an excitation energy source would cause surface atoms to take on an excited state. In the present invention, as a solution to this problem, an AFM not using a laser, namely, a method of detecting displacement of a device surface using a cantilever with a strain gauge adhered thereto. As a solution to the above-mentioned problem that impedes accurate measurement for reasons, such as (1) it is difficult to perform image analysis from signals detected by a plurality of probe tips arranged in a row and (2) the image is contaminated or otherwise damaged by scanning, the present invention provides a single-tip probe dedicated to surface observation, in addition to a multi-tip probe dedicated to surface analysis, and also provides such a mechanism that, during scanning with the surface-observation-dedicated single-tip probe to obtain an observed image, a multi-tip probe serving as the surface-analysis dedicated probe assumes a non-contact state to prevent adhesion of contaminant or other damage, and it is possible for both probes to independently adopt contact or non-contact positions. As this mechanism, a cantilever may be moved upwards and downwards by a temperature-controlled bimetal-type actuator, a comb-shaped electrostatic actuator, or a piezoelectric micro-actuator.

First Embodiment

Figure 1:
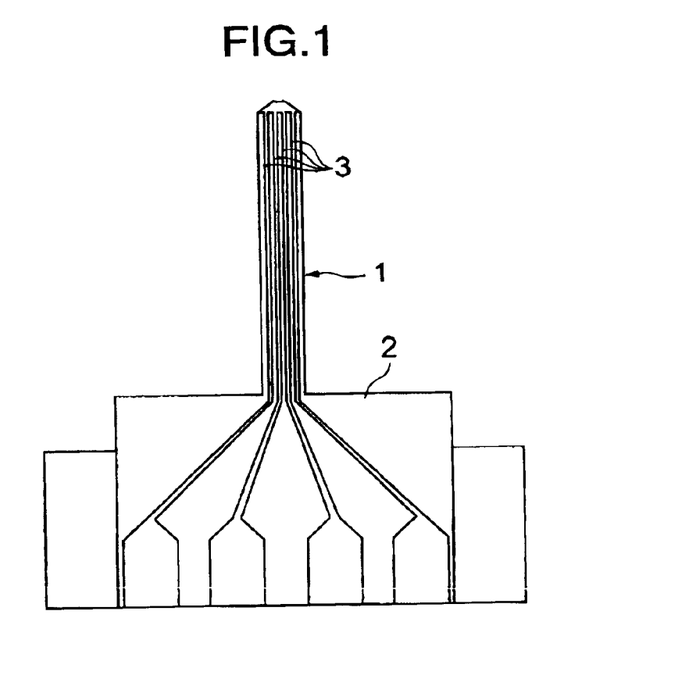
FIG. 1 is a view showing an embodiment according to the present invention in which an elongated cantilever according to the present invention and its base portion are fabricated.

One embodiment will now be described in which a four-tip probe is manufactured by a technique according to the present invention. Using a silicon substrate as a starting material, an elongated cantilever 1 of a 16 μm width, which is shown in FIG. 1, and its base portion 2 are fabricated by lithography. Four lead paths 3 serving as prospective probe tips are patterned in platinum film at distances of 35 μm apart in the base portion 2 and at distances of 3.4 μm apart in the cantilever 1. The material of the lead paths 3 may alternatively be a different metal, such as aluminum or tungsten. The distal end portion of the resultant cantilever 1 is shown in enlarged scale in FIG. 2A. As is understood from FIG. 2a, the distal end portion of the cantilever 1 is tapered and, the individual lead paths 3 formed thereon by patterning extend to and terminate in a shunt area 4 serving as a common conductive portion. Using an FIB apparatus, the resulting distal end portion is microscopically processed to achieve the shaping and processing of four probe tips spaced at sub-micron distances. This sputter etching may include removing only the platinum film or may include removing the platinum film together with silicon substrate portions in a comb-shaped pattern to facilitate contact with a sample surface.

Figure 11:
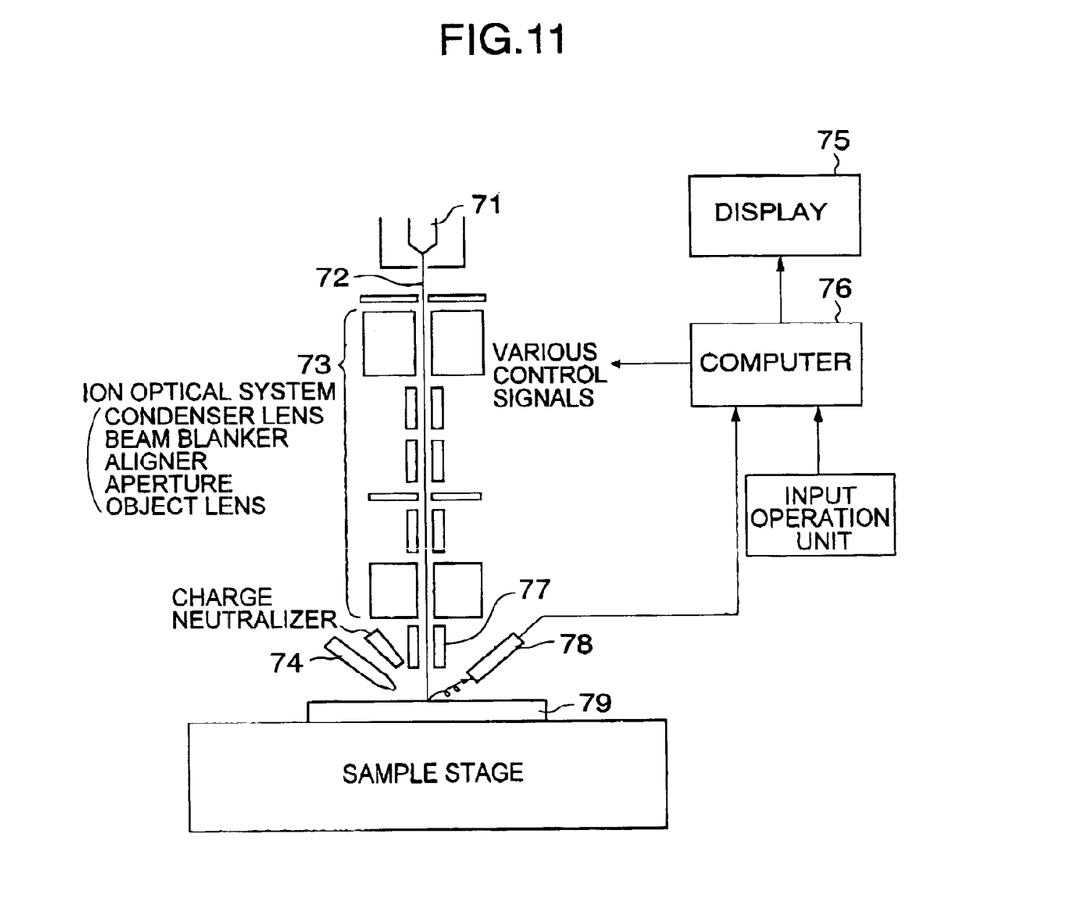
FIG. 11 is a view showing a basic construction of an FIB apparatus used in the present invention.

The basic construction of an FIB apparatus to be used in the present embodiment is shown in FIG. 11. The FIB apparatus focuses ions, which are derived from an ion source 71, into a focused ion beam by an ion optical system 73 and irradiates a sample surface 79 with the focused ion beam 72. As the position to be irradiated is controlled by a deflector 77, electrons or secondary ions are emitted from the irradiated sample surface 79 and then detected by a secondary charged particle detector 78. The detected secondary charged particles are dependent on the sample surface material of an FIM-irradiated beam spot. Therefore, when the irradiated position is scanned two-dimensionally, a microscopic image of the sample surface can be obtained by combining the position information and the detection information by a computer 76 and displaying the result of this combining on a display 75. This is the function of a scanning microscope according to an FIB apparatus. The process in which the material of a sample surface is etched by irradiating the sample surface with the FIB is a sputter etching function, and the process in which the material of a sample surface is etched as a chemical reaction is facilitated by irradiating the FIB to the sample surface while spraying an assist gas from a gas gun 74 is a gas assist etching function. Further, the process in which a material is deposited on a sample surface by irradiating with the FIB while spraying a raw material gas from a gas gun is a Chemical Vapor Deposition (CVD) function.

Figure 2A:
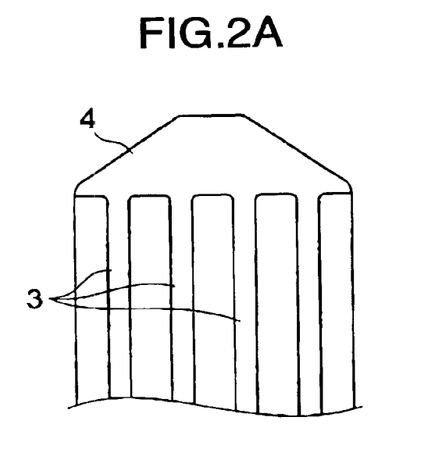
FIG. 2A is an enlarged view of a distal end portion of the cantilever fabricated by lithography.
Figure 2B:
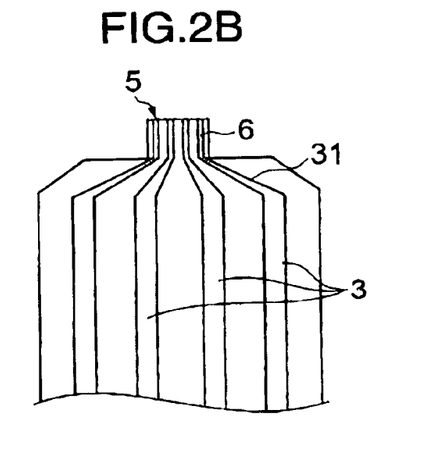
FIG. 2B is a view showing a microscopic probe tip formed by the etching process utilizing an FIB apparatus.

In the present invention, using an FIB apparatus equipped with these functions, a microscopic image of the distal end portion of the above-mentioned cantilever 1 is obtained. As a result, the microscopic image shown in FIG. 2A is obtained. Namely, position information about the distal end portion of the cantilever 1 and pattern information about the shunt area 4 of the distal end portion are obtained. In the present embodiment, on the basis of this position information, the distal end portion is shaped into a rectangular projection 5 of 3.6 μm in width and 2.5 μm in length, as shown in FIG. 2B, using the sputter etching function of the FIB apparatus. Further, using the same sputter etching function of the FIB apparatus, the rectangular projection 5 is processed, and the conductive portion of the shunt area 4 is etched in such a manner that electrodes 6 spaced one from another by 0.8 μm distance are left un-etched. As a result, a microscopic electrodes 6 and lead paths 31, one connecting each microscopic electrode 6 and the respective lead path 3, are formed. By carrying out the sputter etching process of the FIB apparatus, the four-tip probe shown in FIG. 2B is formed on the distal end portion of the cantilever. Alternatively, the same shaping may be achieved by the gas assist etching process of the FIB apparatus instead of the sputter etching process of the FIB apparatus. In this alternative, the assist gas comprises a halogen such as chlorine.

It is possible for the pattern-forming process of the shunt area 4 to be carried out using exposure to X-rays using a stopper, mask aligner, and SOR, or by electron beam rendering and etching.

Second Embodiment

Figure 3:
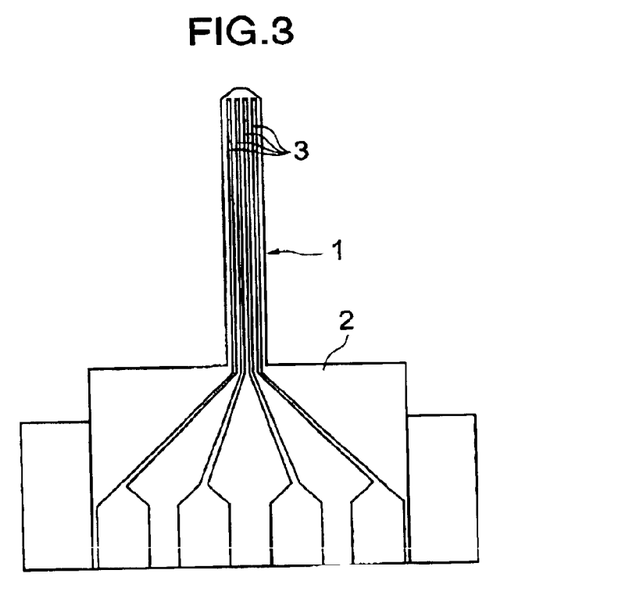
FIG. 3 is a view showing another embodiment in which an elongated cantilever according to the present invention and its base portion are fabricated.

Another embodiment will now be described in which a four-tip probe is manufactured by another deposition technique of the present invention using an FIB apparatus. Using a silicon substrate as a starting material, an elongated cantilever 1 of a 16 μm width, which is shown in FIG. 3, and its base portion 2 are fabricated by lithography. Four lead paths 3, serving as prospective probe tips, are patterned at a spacing of 35 μm in the base portion 2 and at a spacing of 3.4 μm at the cantilever 1. The distal end portion of the resultant cantilever 1 is shown in enlarged scale in FIG. 4A. As is understood from FIG. 4A, the distal end portion of the cantilever 1 is tapered and the individual lead paths 3 formed by patterning extend to and terminate in the distal end portion. The present embodiment is similar to the previous embodiment except that no conductive shunt area is formed. Using an FIB apparatus, the resulting distal end portion is microscopically processed to achieve the shaping and processing of four probe tips spaced at sub-micron distances.

Figure 4A:
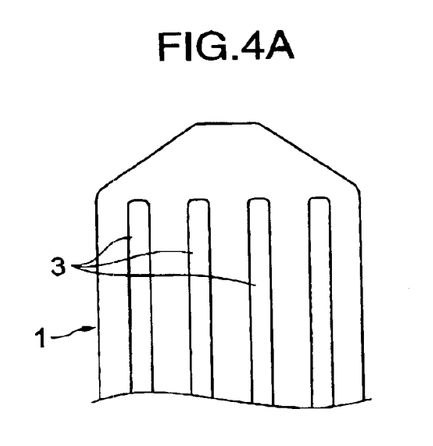
FIG. 4A is an enlarged view of a distal end portion of the cantilever fabricated by lithography.
Figure 4B:
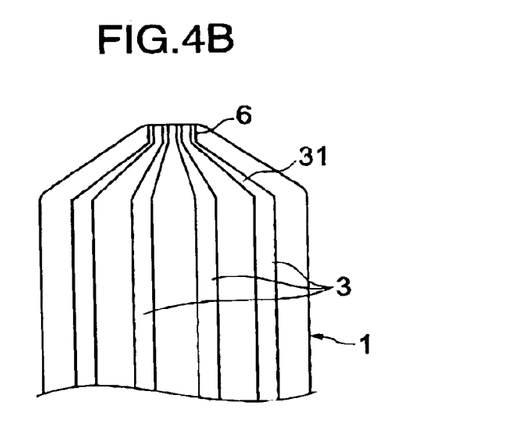
FIG. 4B is a view showing a microscopic probe tip formed by the CVD process according to an FIB apparatus.

In the present embodiment, using an FIB apparatus, a microscopic image of the distal end portion of the above-mentioned cantilever 1 is obtained. As a result, the microscopic image shown in FIG. 4A is obtained. Namely, position information about the distal end portion of the cantilever 1 and position information about the terminal portion of the lead paths 3 at the distal end portion are obtained. In the present embodiment, on the basis of this position information, a conductive portion of the shunt area 4 is deposited on the distal end portion of the cantilever 1 as shown in FIG. 4B, using the CVD function of an FIB apparatus, so as to form electrodes spaced from one another by a distance of 0.8 μm and lead paths 3 connecting parallel microscopic electrodes 6, and the microscopic electrodes 6 and a terminal portion of the respective lead path 3. Using phenanthrene as raw material gas filled in a gas gun, the microscopic electrodes 6 and the lead paths 31 are formed in carbon film on a silicon substrate. Further, the shaping by deposition is carried out in such a manner that the end portions of the microscopic electrodes 6 are extended. Thus, a four-tip probe shown in FIG. 4B is formed on the distal end portion of the cantilever 1 by the CVD process of an FIB apparatus.

Third Embodiment

Figure 5A:
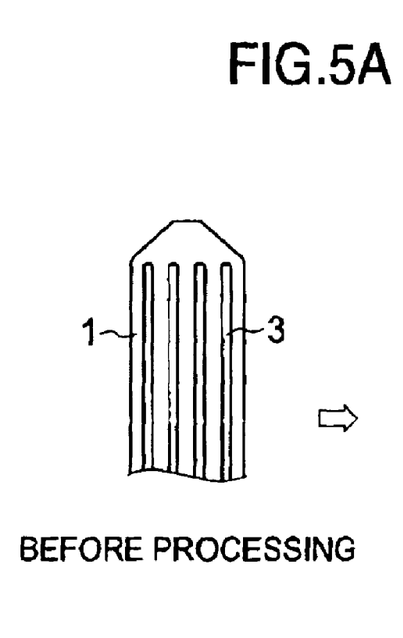
FIGS. 5A–5D are views showing still another embodiment in which vertically directed needle-shaped probe tips are formed on a comb-shaped electrode by the CVD process according to an FIB apparatus.
Figure 5B:
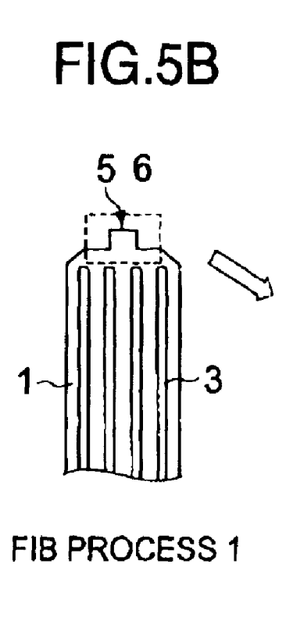
Figure 5C:
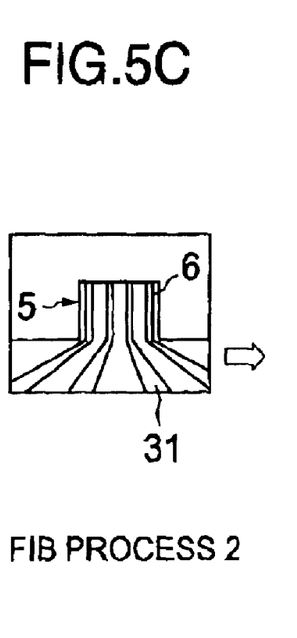
Figure 5D:
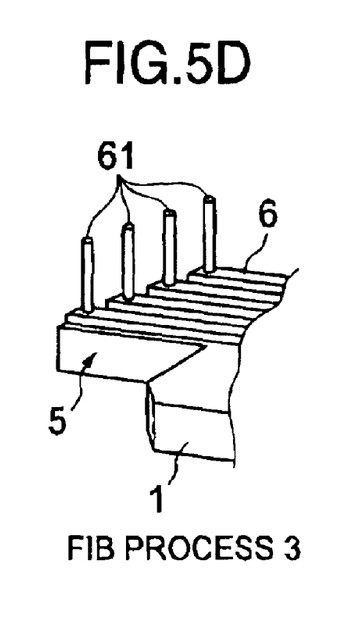

Another embodiment, unlike the previously mentioned embodiment using only a comb-shaped electrode, will now be described in which, in order to improve the ease of contact with a sample, a needle-shaped electrode is formed by laminating and depositing a conductive substance (such as carbon or tungsten) on the distal end portion of each electrode by the CVD process using an FIB apparatus. FIG. 5 shows the processing procedures of the present embodiment, where FIG. 5A shows a state before the processing, and FIGS. 5B, 5C and 5D respectively show the states after FIB processes 1, 2 and 3. As shown the processing procedures of the present embodiment are substantially similar to those of the previously mentioned embodiment with the exception of FIB process 3. Namely, what is shown in FIG. 5A is an elongated cantilever 1 fabricated by lithography and having four-needle lead paths 3 patterned in platinum film. In FIB process 1, the distal end portion of the cantilever 1 is scaled by sputter etching using an FIB apparatus, thereby forming a rectangular projection 5. Notably, this process is not absolutely essential and may be omitted. Namely, the processing procedure may advance to the CVD process as with Embodiment 2, skipping FIB process 1. In FIB process 2, lead paths 31 connecting each microscopic electrode 6 and the respective lead path 3 are microscopically formed on the distal end portion by the CVD process using an FIB apparatus, thereby shaping microscopic electrodes 6 spaced one from another by a sub-micron distance. Then, in FIB process 3, a vertically directed needle 61 is formed on each microscopic electrode 6 of the distal end portion further by the CVD process using an FIB apparatus. Because the thus formed needle 61 contacts a sample surface, the present embodiment can improve the ease of contact with a sample surface as compared to Embodiment 2 using only the comb-shaped electrode. The forming of the vertically directed needle 61 on each microscopic electrode 6 by the CVD process using an FIB apparatus an be applied to the forming of microscopic probe tips 6 in a spaced manner by etching a shunt area 4.

Figure 6A:
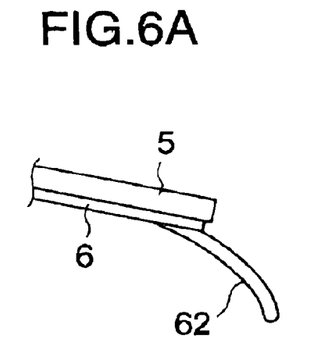
FIG. 6 is a view showing a microscopic probe tip formed in a resilient shape by the CVD process according to an FIB apparatus; A shows a bow type, B shows a coil type.
Figure 6B:
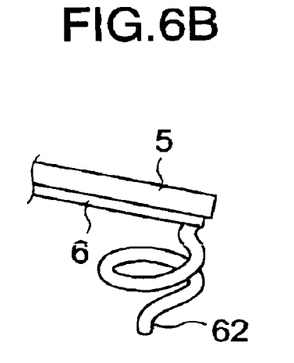

However, the needles 61 of the thus formed four microscopic electrodes 6 would tend to cause erroneous conduction as they cannot uniformly contact a sample due to their various heights, and would tend to cause different contact resistances due to various contact pressures. To avoid these problems, in the present embodiment, the resilient probe 62 is formed in a bow shape shown as electrode in FIG. 6A, thereby having such a resilient structure that uniform contact pressure can be exerted on every probe tip. Alternatively, the shape of the resilient probe 62 may be achieved by a coil shape shown in FIG. 6B. As a result, some variation in height is allowed, so that the ease of manufacture of probe tips can be increased drastically.

Embodiment 4

Figure 7A:
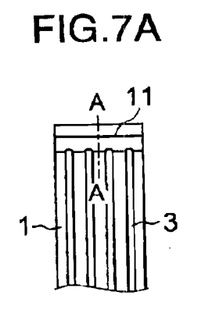
FIGS. 7A–7G are views showing a further embodiment in which a saddle-back-shaped convex bank is formed on a distal end portion of a cantilever to stabilize the contact with a sample.
Figure 7B:
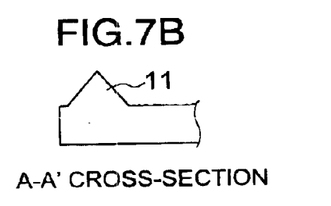
Figure 7C:
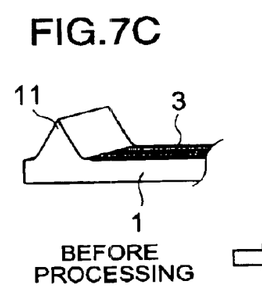
Figure 7D:
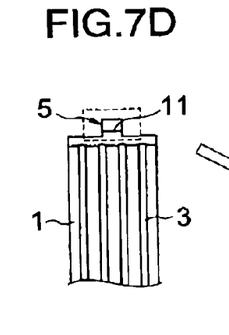
Figure 7E:
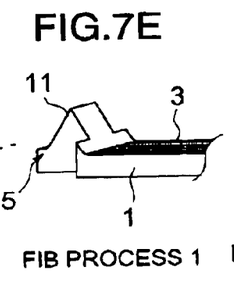
Figure 7F:
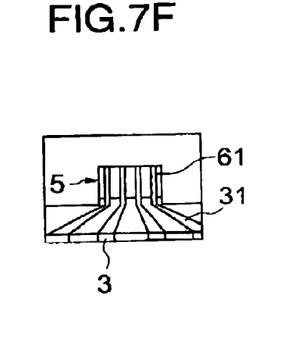
Figure 7G:
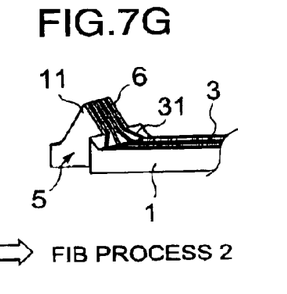

A still further embodiment will now be described in which, when an elongated cantilever 1 is fabricated by lithography, a convex bank 11 is formed on the distal end portion of the cantilever 1 and four-probe-tip lead paths 3 are patterned in platinum film on the resulting cantilever 1, thereby causing uniform contact pressure to be exerted on every probe tip. FIGS. 7A–7G show this processing procedure. What is shown prior to processing is the cantilever 1 fabricated by lithography. A cross-sectional view taken along A–A' that is a plan view of FIG. 7A is shown in FIGS. 7D and 7E, the bank 11 being the distal end portion of the cantilever 1 is partially scaled by sputter etching using an FIB apparatus, thereby forming a rectangular projection 5. As is noted from FIG. 7E, in the resulting cantilever 11, a saddle-back-shaped convex bank 11 is left un-scaled on the rectangular projection 5. In FIB process 2 shown in FIG. 7F and FIG. 7G, lead paths 31 connecting each microscopic electrode 6 and the respective lead path 3 are microscopically formed on the distal end portion by the CVD process using an FIB apparatus, thereby forming four probe tips spaced one after another by a sub-micron distance. As is apparent from FIG. 7G, the microscopic electrodes 6 are deposited on the surface of the saddle-back-shaped convex bank 11 and hence have a saddle-back shape. Therefore, when the resulting cantilever 1 is brought close to a sample surface, the crest of the saddle-back comes into contact with the sample surface. In the case of the present embodiment, if the crest of the bank 11 at the distal end portion of the cantilever 1 is uniformly formed as the original cantilever 1 is fabricated by lithography, the convex portion of the microscopic electrodes 6 also are uniform in height, thereby causing a stabilized contact relation between the sample surface and the plural microscopic electrodes 6. Alternatively, the bank 11 at the distal end portion of the cantilever 1 may be formed by reactive dry etching or wet etching. Further, the forming of such a bank 11 on the distal end portion of the cantilever 1 can be applied to the forming of the cantilever having on its distal end portion a shunt area 4.

Embodiment 5

Figure 8:
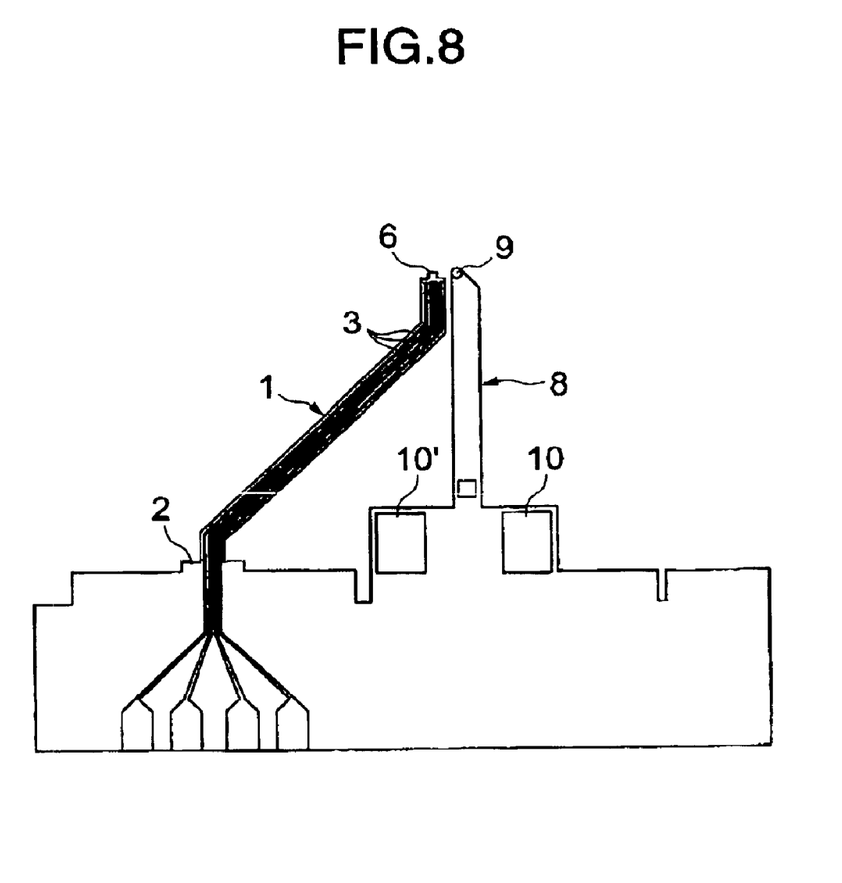
FIG. 8 is a view showing another embodiment in which a cantilever having on its distal end portion four analysis-dedicated microscopic probe tips and an A cantilever having on its distal end portion an AFM probe tip are juxtaposed in a manner that the respective probe tips are close to each other.
Figures 9A, 9B, 9C, 9D:
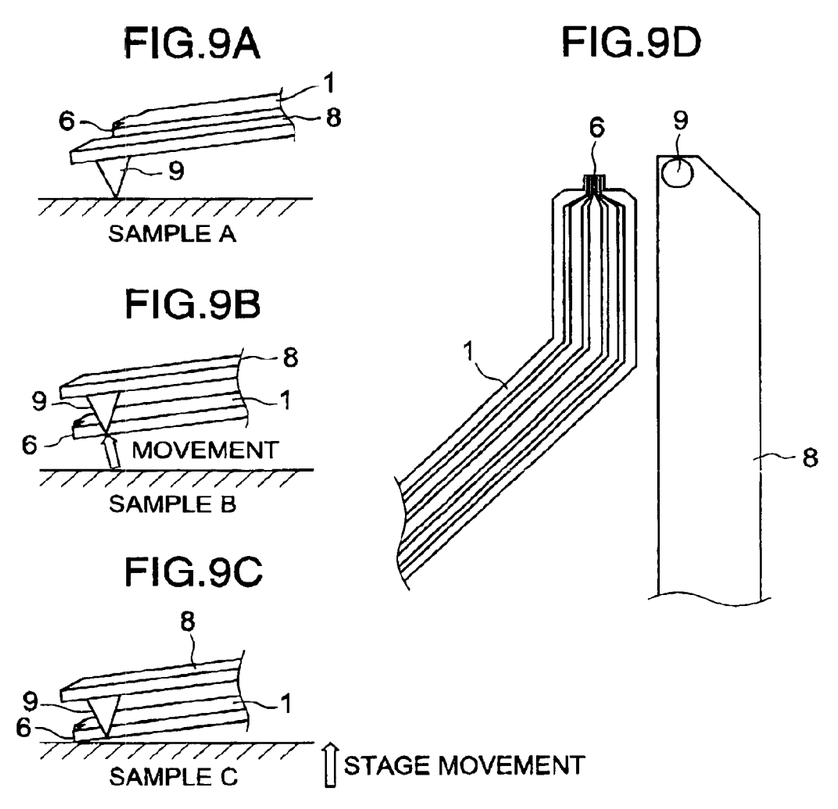
FIG. 9A is a view showing a relation of contact in which the four analysis-dedicated microscopic probe tips and the AFM probe tip are in contact with a sample.
FIG. 9B is a view showing the AFM probe tip moved to a raised position.
FIG. 9C is a view showing the four microscopic probe tips in contact with the sample.
FIG. 9D is an enlarged view of the distal end portions of the two cantilevers.

An embodiment of a surface characteristic analysis apparatus according to the present invention will now be described in which the apparatus is equipped with a probe of an atomic force microscope (AFM) so as to have a function of positioning the measuring point on an object surface. As shown in FIG. 8, a cantilever 1 having on its distal end portion four microscopic analyzing probe tips 6 and an AFM cantilever 8 having on its distal end portion AFM probe tips 9 are juxtaposed in such a manner that the probe tips are close to the probe tips 9. The distal end portions of the two juxtaposed cantilevers are shown, on an enlarged scale, in FIG. 9D. As is noted from FIG. 8, in the present invention, a pair of pads 10, 10' are formed one on each side of the base portion of the AFM cantilever 8. When the pads 10, 10' are heated, the AFM cantilever 8 is retracted upward by a bimetal effect. While the pads 10, 10' are not heated, the distal end portions of the AFM probe tips 9 come into contact with a sample surface and, at that time, the distal end portions of the four microscopic probe tips 6 are moved away from the sample surface. To keep this posture, it is essential to select the heights of the AFM probe tips 9 to meet the undulation of a sample. Generally, 5 $\mu$m to 20 $\mu$m is appropriate for the heights. When the pads 10, 10' are heated to retract the cantilever 8 upward by bimetal effect, the distal end portions of the AFM probe tips 9 are retracted to a position above the distal end portions of the four microscopic probe tips 6 as shown in FIG. 9B. At that time, the distal end portions of both the probe tips 6, 9 assume a non-contact state with respect to a sample surface. Then, by moving a sample stage (not shown) in the Z (upward) direction, an adjustment is made in such a manner that the four microscopic probe tips 6 comes into contact with the sample at an appropriate pressure, as shown in FIG. 9C. The contact pressure at that time is detected by a strain gauge mounted on the cantilever 1. The amount of displacement to retract must be the height of the probe tip 9+$\alpha$. Generally, $\alpha$ is over 1 $\mu$m. This is true because, when the four microscopic probe tips 6 are brought into contact with a sample surface at a predetermined pressure, possible deformation of the cantilever 1 is considered. If the AFM-cantilever detection method is of a self-detection type in which a strain gauge is built in the cantilever body instead of the light leverage method using laser light, possible errors due to excitation in this detection and the retraction of the distal end portion can be avoided by observation and measurement in dark field. Further, as a secondary effect, according to the conventional light leverage method, in the case of, for example, a multi-cantilever structure like the present embodiment, laser position detection systems equal or near in number to the plural cantilevers are required, which would be very complex in apparatus construction and very meticulous and laborious in use such as laser positioning. On the contrary, according to the self-detection method, the apparatus can be constructed with maximum ease, only requiring a plurality of electrical signal outputs.

The operation of the apparatus according to the present embodiment will now be described. Firstly, the cantilevers assume a non-heated state, namely, the distal end portion of the AFM probe tip 9 are brought into contact with a sample surface and the distal end portions of the four microscopic probe tips 6 are brought away from the sample surface. In this state, the sample surface is scanned two-dimensionally to obtain a three-dimensional image of the sample surface. This operation is similar to that of the ordinary scanning probe microscope. The sample's position to be measured is selected and specified from the obtained three-dimensional image in such a manner that the distal end portions of the four probe tips 6 comes to a designated position. Because the distal end portions of the four microscopic probe tips 6 are spaced a predetermined distance from the distal end portion of the AFM probe tip 9, such drift has to be corrected on the coordinate. The sample stage is driven in X and Y directions in such a manner that the distal end portion of the AFM probe tip 9 comes to a position deviated from the specified measured position by the amount of the drift. As a result, the distal end portions of the four probe tips 6 come to the designated position. Subsequently, the pads 10, 10' are heated as shown in FIG. 9B to cause the cantilever 8 to retract upward and, then, the sample stage is moved in the Z (upward) direction to make an adjustment such that the four microscopic probe tips 6 come into contact with the sample at an appropriate pressure. The contact pressure at that time is monitored by the strain gauge mounted on the cantilever 1. When it is recognized that a constant pressure is exerted on the sample, the four-probe-tip measurement is started to obtain data at that position.

Advantageous Results

The micro cantilever manufacturing method according to one aspect of the present invention comprises the steps of fabricating a cantilever having a plurality of lead portions spaced one from another and a shunt area formed at a distal end portion of the cantilever by a micro cantilever fabrication technique utilizing lithography, and forming a probe on the cantilever by processing the shunt area of the distal end portion of the cantilever by sputtering or gas assist etching using a beam of focusing charged particles. According to another aspect of the present invention, the method comprises the steps of fabricating a cantilever having a plurality of lead portions spaced one from another, by a micro cantilever fabrication technique utilizing lithography, and forming a probe on the cantilever by CVD which irradiates a beam of focused charged particles to the distal end portion of the cantilever while spraying a gas of raw material thereto. Therefore, it is possible to easily obtain electrical information of microscopic portions and ultra-surface, which was impossible in the conventional art. In the method of manufacturing a microscopic multi-probe according to the present invention, because the probe tips are formed into a resilient structure by CVD, some variation in height of the probe tips are allowed, thereby increasing the easiness of the probe tip fabrication drastically.

The surface characteristic analyzing apparatus according one aspect of the present invention comprises first a micro cantilever having on its distal end portion a microscopic multi-tip probe, an AFM-dedicated micro cantilever having on its distal end portion a dedicated microscopic multi-tip probe; the AFM-dedicated micro cantilever being spaced by a known, predetermined distance from the first micro-cantilever, and means for driving the two micro cantilevers independently of each other into contact/non-contact states with respect to a sample. Therefore, the apparatus has the functions of obtaining an observed imaged of a sample surface by an AFM with the microscopic multi-tip probe in a non-contact state, determining a measuring region from the observed image, positioning the microscopic multi-tip probe in the determined measuring region and bringing the microscopic multi-tip probe into contact with the determined measuring region. Even in electricity measurement at an arbitrary position (e.g., a wiring portion) where positioning was difficult to take place on a conventional optical microscope, accurate measurement of electricity can be achieved by an array probe that can be combined with AFM. Further, the means for driving the cantilevers between a contact state and a non-contact state can be achieved with ease by employing a temperature-controlled bimetal-type actuator, a comb-shaped electrostatic actuator, or a piezo-electric micro-actuator. Furthermore, by using the self-detection method in which a strain gauge is mounted on the cantilever, electricity measurement in perfect dark field can be realized.

What is claimed is:

1. A method of manufacturing a multi-tip probe comprising the steps of:
    forming a cantilever using photolithographic techniques;
    forming a plurality of lead portions along the cantilever and which terminate in a conductive shunt area at a distal end of the cantilever; and
    forming a plurality of electrodes at the conductive shunt area by sputtering or gas-assisted etching of the conductive shunt area using a focused charged particle beam.

2. A method of manufacturing a multi-tip probe according to claim 1; wherein the plurality of electrodes are spaced apart from one another at a spacing of less than one micron.

3. A method of manufacturing a multi-probe according to claim 1; further comprising the step of forming a needle-shaped probe on a distal end of each of the electrodes by chemical vapor deposition using a focused ion beam device.

4. A method of manufacturing a multi-tip probe according to claim 3; wherein the step of forming a needle-shaped probe further comprises the step of forming the needle-shape probe with a curved structure so as to have resilience.

5. A method of manufacturing a multi-tip probe according to claim 1; wherein the step of forming the cantilever using photolithographic techniques includes the step of forming a convex portion at the distal end of the cantilever; and the step of forming a plurality of electrodes on the cantilever comprises forming the plurality of electrodes on the convex portion.

6. A method of manufacturing a multi-tip probe comprising the steps of:
    forming a cantilever using photolithographic techniques;
    forming a plurality of lead portions along the cantilever; and
    forming a plurality of electrodes at the distal end of the cantilever by irradiating the distal end of the cantilever with a focused charged particle beam while blowing a source gas toward the distal end.

7. A method of manufacturing a multi-tip probe comprising the steps of:
    providing a cantilever having a distal end portion on which is formed a conductive film; and
    dividing the conductive film into a plurality of electrodes by sputter etching or gas-assisted etching of the conductive film using a focused charged particle beam thereby forming a multi-tip probe.

8. A method according to claim 7; wherein the plurality of electrodes have distal ends spaced apart less than one micron from one another.

9. A method according to claim 8; wherein the providing step comprises providing a cantilever, and forming a plurality of conductive film lead portions extending lengthwise along the cantilever and terminating at a distal end portion thereof in a common conductive film.

10. A method according to claim 9; wherein the conductive film lead portions and the common conductive film are formed by lithography.

11. A method according to claim 9; further comprising the step of forming a needle-shaped probe on a distal end of each of the electrodes.

12. A method according to claim 11; wherein each needle-shaped probe has a curved shape.

13. A method according to claim 9; wherein the dividing step comprises dividing the common conductive film into a plurality of electrodes by sputter etching the common conductive film using a focused charged particle beam.

14. A method according to claim 9; wherein the dividing step comprises dividing the common conductive film into a plurality of electrodes by sputter etching the common conductive film using a focused charged particle beam while directing an assist gas toward the distal end portion of the cantilever.

15. A method according to claim 8; wherein the plurality of electrodes comprises four electrodes.

16. A method according to claim 8; wherein the conductive film is formed of one of platinum, aluminum and tungsten.

17. A method according to claim 7; wherein the providing step comprises providing a cantilever, and forming a plurality of conductive film lead portions extending lengthwise along the cantilever and terminating at a distal end portion thereof in a common conductive film.

18. A method according to claim 17; wherein the conductive film lead portions and the common conductive film are formed by lithography.

19. A method according to claim 7; further comprising the step of forming a needle-shaped probe on a distal end of each of the electrodes.

20. A method according to claim 19; wherein each needle-shaped probe has a curved shape.

21. A method according to claim 7; wherein the dividing step comprises dividing the common conductive film into a plurality of electrodes by sputter etching the common conductive film using a focused charged particle beam.

22. A method according to claim 7; wherein the dividing step comprises dividing the common conductive film into a plurality of electrodes by sputter etching the common conductive film using a focused charged particle beam while directing an assist gas toward the distal end portion of the cantilever.

23. A method according to claim 7; wherein the electrodes extend generally parallel to one another and are spaced apart from one another at a spacing less than one micron.

24. A method of manufacturing a multi-tip probe comprising the steps of:
    providing a cantilever having a distal end portion;
    forming a plurality of conductive lead portions extending lengthwise along the cantilever; and
    forming a plurality of electrodes on the distal end of the cantilever and in contact with respective ones of the conductive lead portions by irradiating the distal end portion of the cantilever with a focused charged particle beam while directing a source gas toward the distal end portion thereby forming a multi-tip probe.

25. A method according to claim 24; wherein the plurality of electrodes have distal ends spaced apart less than one micron from one another.

26. A method according to claim 25; further comprising the step of forming a needle-shaped probe on a distal end of each of the electrodes.

27. A method according to claim 26; wherein each needle-shaped probe has a curved shape.

28. A method according to claim 24; wherein the plurality of electrodes comprises four electrodes.

29. A method according to claim 24; wherein the electrodes extend generally parallel to one another and are spaced apart from one another at a spacing less than one micron.

* * * * *